(12) United States Patent
Eidenschink

(10) Patent No.: US 7,485,140 B2
(45) Date of Patent: Feb. 3, 2009

(54) BIFURCATION STENT ASSEMBLY

(75) Inventor: Tracee Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 426 days.

(21) Appl. No.: 11/155,155

(22) Filed: Jun. 17, 2005

(65) Prior Publication Data
US 2006/0287712 A1 Dec. 21, 2006

(51) Int. Cl.
A61F 2/06 (2006.01)
(52) U.S. Cl. .................. 623/1.15; 623/1.35
(58) Field of Classification Search .......... 623/1.11, 623/1.16, 1.21, 1.35, 1.44, 1.37, 1.24, 1.28, 623/1.15
See application file for complete search history.

(56) References Cited

U.S. PATENT DOCUMENTS

| | | | | |
|---|---|---|---|---|
| 4,906,244 | A | 3/1990 | Pinchuck et al. | 606/194 |
| 5,500,181 | A | 3/1996 | Wang et al. | 264/532 |
| 5,922,021 | A | 7/1999 | Jang | 623/1 |
| 6,123,721 | A | 9/2000 | Jang | 623/1 |
| 6,210,429 | B1 | 4/2001 | Vardi et al. | 623/1.11 |
| 6,235,053 | B1 | 5/2001 | Jang | 623/1.15 |
| 6,261,319 | B1 | 7/2001 | Kveen et al. | 623/1.15 |
| 6,325,826 | B1 | 12/2001 | Vardi et al. | 623/1.35 |
| 6,334,870 | B1 | 1/2002 | Ehr et al. | 623/1.16 |
| 6,348,065 | B1 | 2/2002 | Brown et al. | 623/1.16 |
| 6,471,720 | B1 | 10/2002 | Ehr et al. | 623/1.15 |
| 6,478,816 | B1 | 11/2002 | Kveen et al. | 623/1.15 |
| 6,524,336 | B1 * | 2/2003 | Papazolgou et al. | 623/1.35 |
| 6,676,699 | B2 * | 1/2004 | Shiu | 623/1.24 |
| 6,695,877 | B2 * | 2/2004 | Brucker et al. | 623/1.16 |
| 6,706,062 | B2 | 3/2004 | Vardi et al. | 623/1.15 |
| 6,746,479 | B2 | 6/2004 | Ehr et al. | 623/1.16 |
| 6,818,014 | B2 | 11/2004 | Brown et al. | 623/1.16 |
| 6,835,203 | B1 | 12/2004 | Vardi et al. | 623/1.34 |
| 7,220,275 | B2 * | 5/2007 | Davidson et al. | 623/1.35 |
| 2002/0013618 | A1 * | 1/2002 | Marotta et al. | 623/1.15 |
| 2002/0042650 | A1 * | 4/2002 | Vardi et al. | 623/1.35 |
| 2003/0055483 | A1 | 3/2003 | Gumm | 623/1.11 |
| 2004/0133268 | A1 | 7/2004 | Davidson et al. | 623/1.35 |
| 2004/0215327 | A1 * | 10/2004 | Doig et al. | 623/1.16 |

(Continued)

FOREIGN PATENT DOCUMENTS

EP 0 904 745 3/1999

(Continued)

Primary Examiner—Todd E Manahan
Assistant Examiner—Thomas McEvoy
(74) Attorney, Agent, or Firm—Vidas, Arrett & Steinkraus

(57) ABSTRACT

A stent assembly comprises a stent and a side branch flap. The stent has a substantially tubular body which defines a primary lumen and is comprised of a plurality of interconnected stent members. Adjacent stent members define a plurality of stent openings that extend through the body and which are in fluid communication with the primary lumen. At least one stent opening is a side branch opening. The side branch flap is a non-tubular body having a planar structure. A first region of the planar structure is overlappingly positioned across a portion of the side branch opening prior to deployment. A second region of the planar structure is engaged to a portion of the body of the stent immediately adjacent to the perimeter of the side branch opening. When the assembly is deployed the first region of the flap is displaced radially outward from the side branch opening.

15 Claims, 8 Drawing Sheets

U.S. PATENT DOCUMENTS

2004/0243219 A1* 12/2004 Fischer et al. .............. 623/1.15
2005/0059923 A1*  3/2005 Gamboa ..................... 604/9
2007/0067019 A1*  3/2007 Miller et al. ............... 623/1.16
2007/0106375 A1*  5/2007 Vonderwalde .............. 623/1.35

FOREIGN PATENT DOCUMENTS

WO    WO 2004/026180    4/2004

* cited by examiner

BIFURCATION STENT ASSEMBLY

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Description of the Related Art

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Within the vasculature it is not uncommon for stenoses to form at a vessel bifurcation. A bifurcation is an area of the vasculature or other portion of the body where a first (or parent) vessel is bifurcated into two or more tubular component vessels. Where a stenotic lesion or lesions form at such a bifurcation, the lesion(s) can affect only one of the vessels (i.e., either of the tubular component vessels or the parent vessel) two of the vessels, or all three vessels.

Many of the bifurcated stents that have been disclosed are segmented, and include a primary branch and at least one secondary branch which is positioned adjacent to and/or partially within the primary branch. Often such segmented systems employ multiple catheters and/or balloons to deploy all of the stent segments. Other bifurcated stents include single structure stents wherein the stent is comprised of a trunk with two or more branches extending therefrom. Still other stent configurations employ a single substantially tubular stent which has a specialized side-branch opening through which an additional stent or structural component may be deployed.

In spite of the many bifurcated stents that have been disclosed, there remains a need for a stent suitable for treatment of a vessel bifurcation wherein the side branch vessel is provided with improved coverage particularly in the region of the contra-lateral wall, opposite the carina, without the added strain typically associated with standard tubular structures.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the present invention is directed to a stent assembly comprising a stent. The stent has a tubular body which defines a primary flow path or lumen therethrough. The body of the stent is made up of any of a variety of patterns of interconnected strut members, connecting members, etc. The pattern of struts and/or connectors of the body define a plurality of cells or openings through the body wall. At least one of the cells is a specialized opening, which provides fluid communication between the primary lumen of the stent and a branch vessel of a vessel bifurcation.

In some embodiments, exemplary configurations of a pattern that the stent body may include, are shown and/or described in the following U.S. Pat. Nos. 6,746,479, 6,478,816, 6,471,720, 6,334,870, 6,261,319, 6,818,014, 6,348,065, 5,922,021, 6,235,053, and 6,123,721, the entire contents of each of which are incorporated herein by reference.

In some embodiments, exemplary configurations, shapes, sizes, etc. of a side branch opening that the stent may include are shown and/or described in the following U.S. Patents and publications: U.S. Pat. Nos. 6,835,203, 6,706,062, 6,325,826, 6,210,429, and 2003-0055483-A1, the entire contents of each of which are incorporated herein by reference.

As indicated, the references cited above are provided to illustrate some examples of stent patterns and cell configurations suitable for use in the present invention. The invention is not limited to the examples cited and may include combinations of patterns and configurations which can include those disclosed above, as well as others.

In some embodiments of the invention the stent is part of a stent assembly which includes a stent and at least one secondary piece or flap. In at least one embodiment the flap(s) is a planar (rather than a tubular) structure which is positioned immediately adjacent to the side branch opening of the stent. In at least one embodiment the flap is defined by a pattern of interconnected struts or members which define a plurality of openings or cells therethrough. The pattern of the flap may be similar or different to that of the stent body.

In at least one embodiment the flap has two dimensional shape similar to that of a truncated cone.

In some embodiments the flap comprises three regions: two side regions and a medial region in between. In at least one embodiment the pattern of the side regions are similar to one another whereas the pattern of the medial region is different than that of the side regions. The patterns may differ by providing the regions with different materials, different strut configurations, different cell sizes and shapes, etc.

In some embodiments the flap is at least partially overlapped by the body of the stent. When preparing the stent assembly for use the flap is initially positioned upon a delivery catheter and the stent is then placed over the flap such that the flap is substantially positioned across the side branch opening. In at least one embodiment, at least three edges of the flap remain engaged to the body of the stent adjacent to the side branch opening when the assembly is in the fully expanded or deployed state.

In at least one embodiment, when the assembly is in the deployed state, at least a portion of the flap is pushed outward from the circumferential plane of the stent to engage or be positioned adjacent to the contra-lateral wall of a side branch vessel. Other configurations of the stent and flap are included in embodiments of the invention. For example, the flap may be engaged to the distal aspect of the side branch opening of the stent, for positioning adjacent to the carina when deployed. In some embodiments multiple flaps may be utilized at the side branch opening to provide complete or near-complete coverage of the ostium of the side branch vessel.

In some embodiments the flap is constructed from one or more wires woven or otherwise formed into the desired pattern of members which define the flap. In some embodiments the pattern of the flap is provided by cutting the flap from a sheet of suitable stent material, in accordance with a desired pattern; molding the flap, wherein the mold defines the desired pattern; is cut from a tubular member, etc.

These and other embodiments which characterize the invention are pointed out with particularity in the claims annexed hereto and forming a part hereof. However, for a further understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
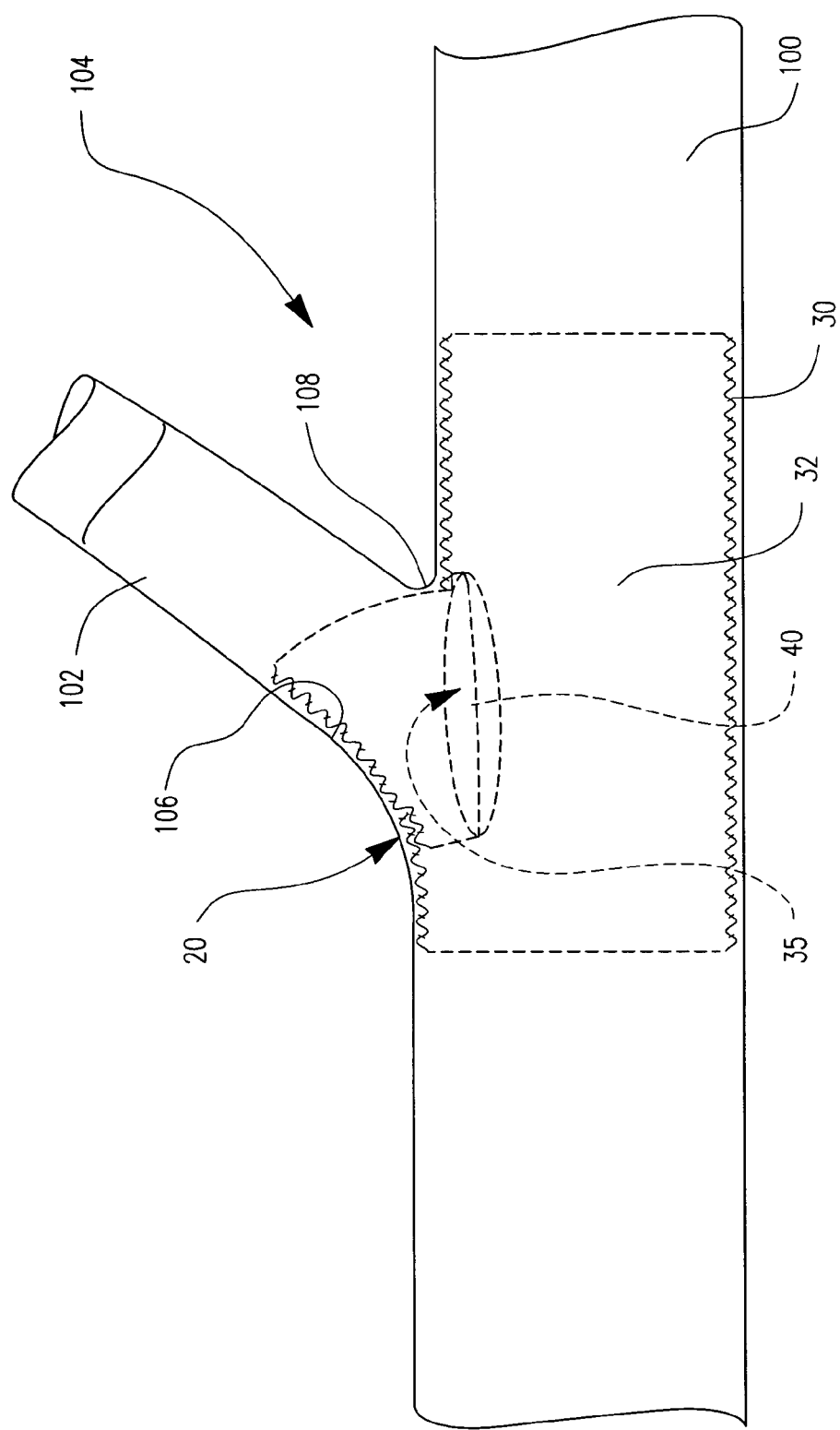
FIG. 1 is a longitudinal side, cross-sectional view of an embodiment of the invention shown in the environment of a vessel bifurcation prior to deployment of the assembly.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Referring now to the drawings which are for the purposes of illustrating embodiments of the invention only and not for purposes of limiting same, in the embodiment shown in FIG. 1, a stent delivery system 10 is shown, having a catheter 12, which is configured to deliver a stent assembly 20 to a bifurcation 104 of vessels, such as the primary vessel 100 and secondary vessel 102 shown.

The stent assembly 20 is comprised of a primary framework or stent 30 and a side branch member or flap 40.

Figure 2:
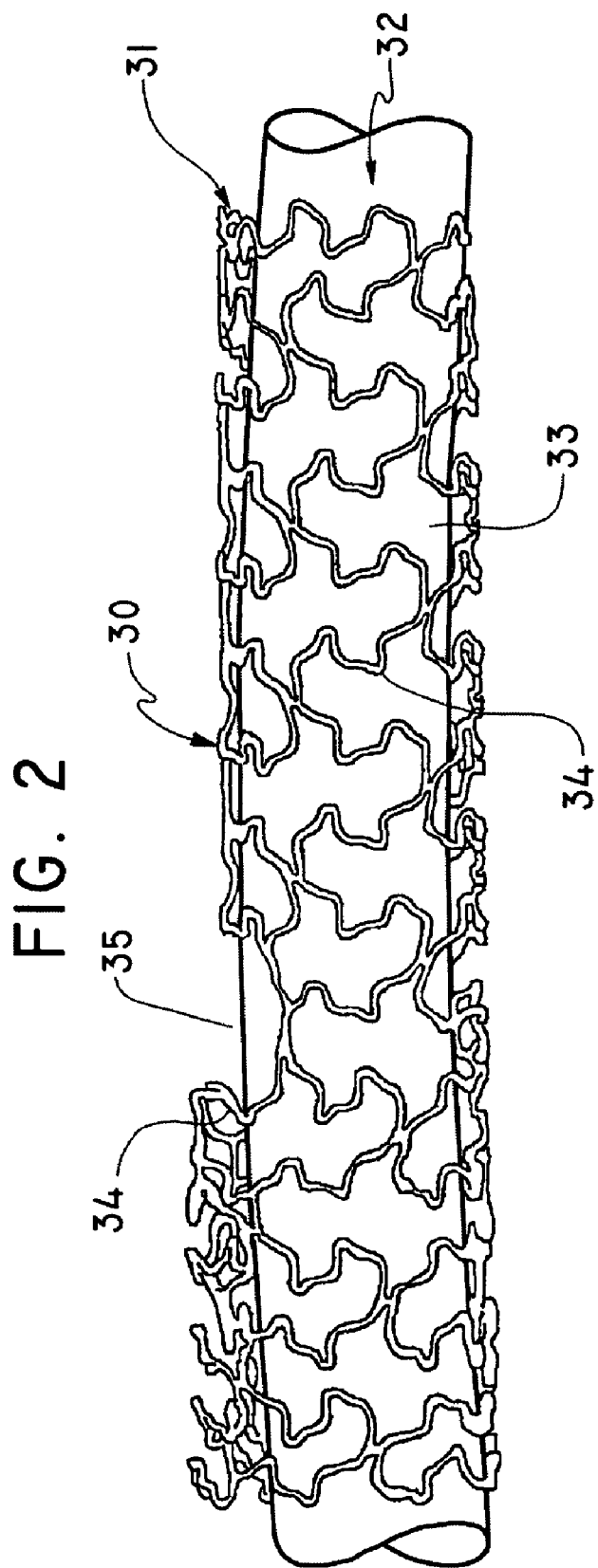
FIG. 2 is a perspective view of a stent of the type shown in FIG. 1

An embodiment of the stent 30 is illustrated in FIG. 2. The stent may be any type or configuration of stent desired. The example shown in FIG. 2 is comprised of a substantially hollow tubular body 31 which defines an stent lumen 32 open at both ends of the stent. The body 31 is made up of a plurality of interconnecting stent members 34 of which adjacent members 34 define openings or cells 33 which extend through the body 31 and are in communication with the lumen 32.

The members 34 may have any of a variety or lengths, widths, thicknesses, etc. Members 34 may be curved, straight, bent, and/or otherwise configured. In some embodiments members 34 are characterized as struts, connectors, bands, and/or other stent structures, and arranged accordingly. The cells 33 defined by the members 34 may likewise have any of a variety of sizes, shapes, and/or configurations as desired.

In at least one embodiment the cells 33 and members 34 are configure to provide the body 31 with a somewhat regular or visually recognizable pattern or geometry.

Figure 7:
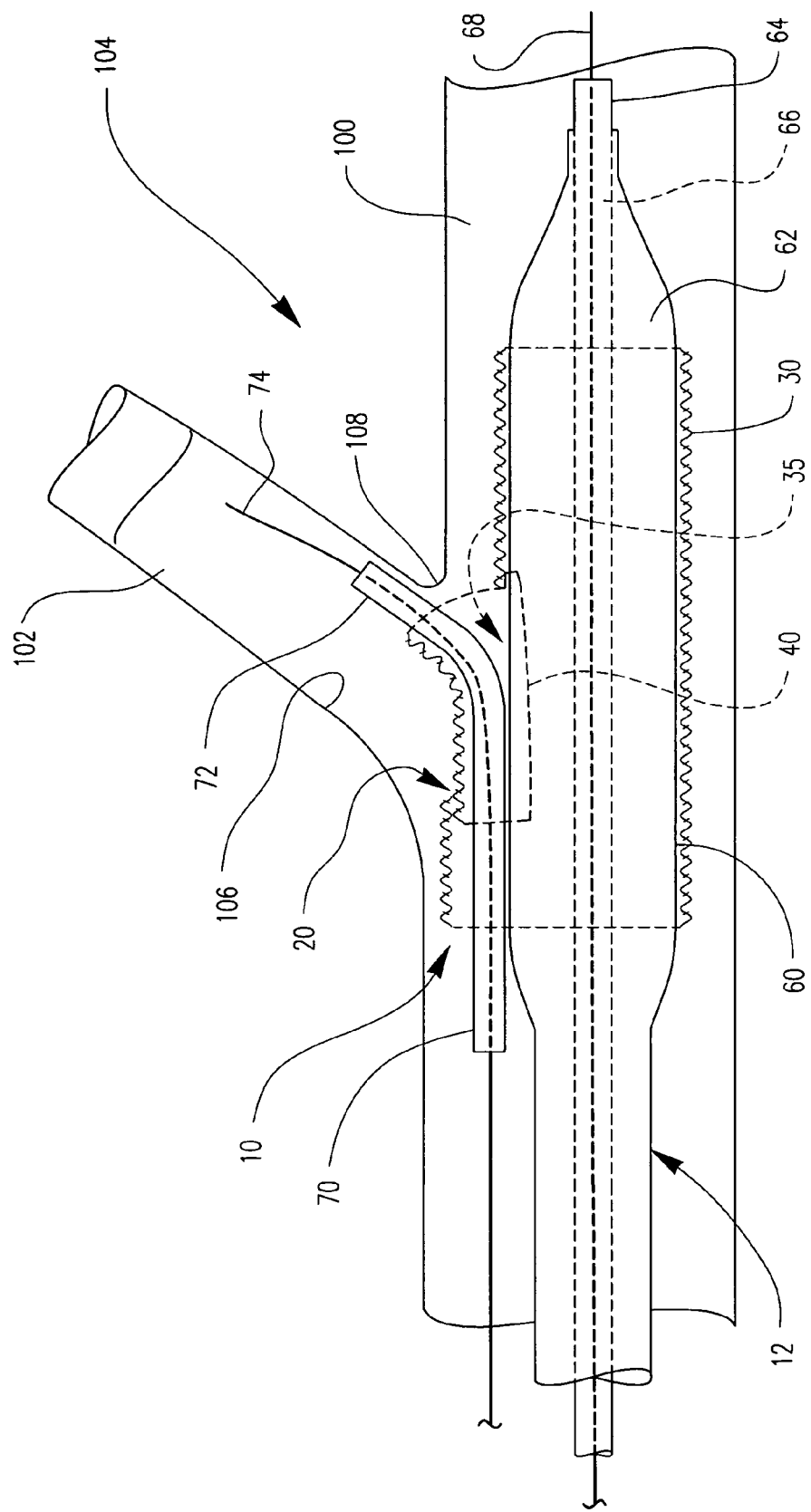
FIG. 7 is a longitudinal side, cross-sectional view of the assembly shown is FIG. 6 following its deployment at a vessel bifurcation and withdrawal of the delivery system.

In the various embodiments however, one of the cells 33 is a specialized cell which provides the stent lumen 32 with fluid communication to the side branch vessel 102 of the bifurcation 100, such as in the manner shown in FIG. 7. This specialized cell or side-branch opening 35 is often a cell which has a different shape and/or size than the remaining cells 33, and in at least one embodiment opening 35 will have a greater area than at least some of the cells 33 adjacent thereto. The particular physical dimensions of the side branch opening 35 will often depend on the specific anatomy of the bifurcation, and as such its characteristics are highly variable.

In the various embodiments shown and described herein, the flap 40 is configured to be engaged to the stent 30 both before and after deployment, wherein at least a portion of the flap 40 in the deployed state extends radially outward from the side branch opening 35 to engage, or be positioned adjacent to, the contra-lateral wall 106 (opposite the carina 108) of the secondary vessel 102.

Figure 8:
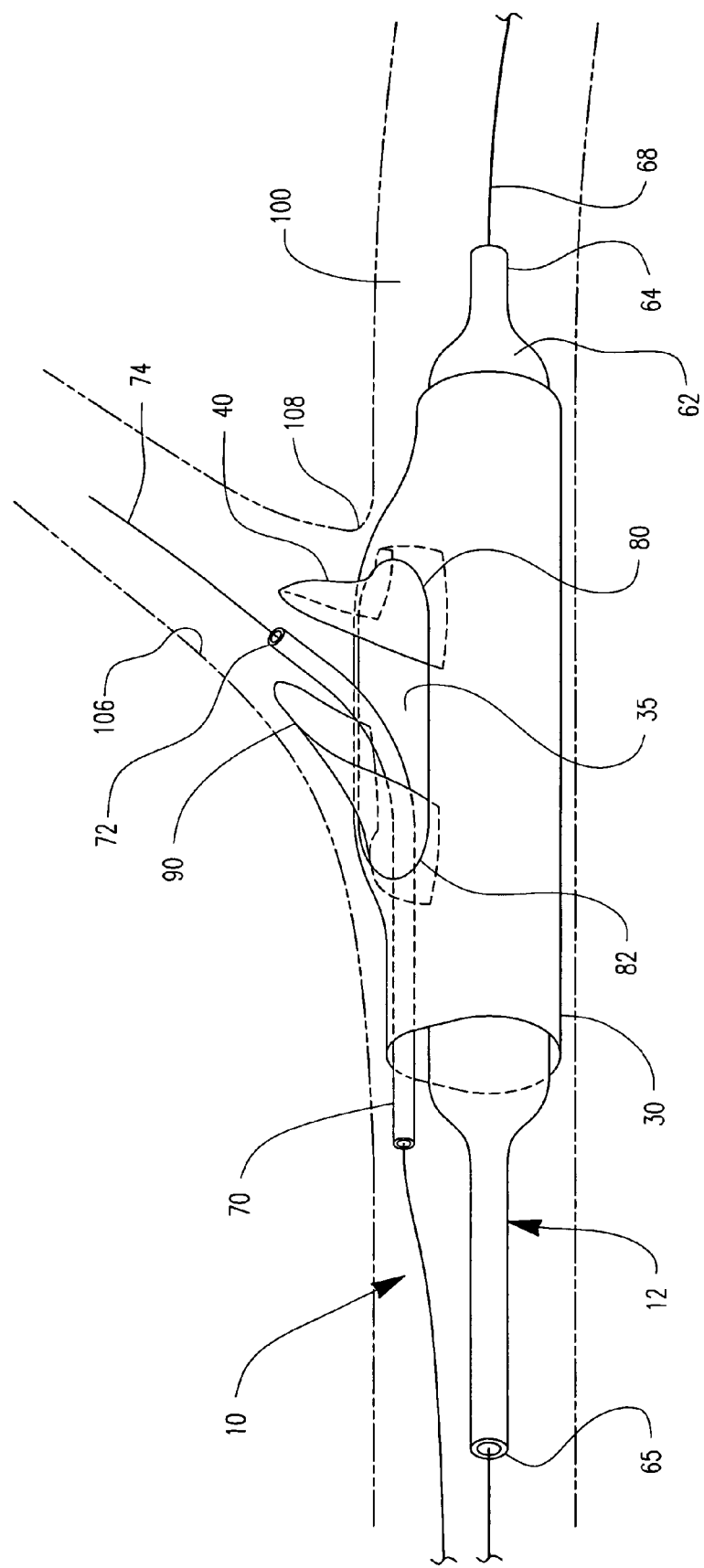
FIG. 8 is a partial perspective view of an embodiment of the invention shown in its environment of use.

In some embodiments when the flap 40 engages the distal aspect, or side 80, of the side branch opening of the stent, for positioning adjacent to the carina 108 when deployed. In some embodiments multiple flaps 40 may be utilized at the side branch opening 35 to provide complete or near-complete coverage of both the contra-lateral wall 106 and the carina 108, such as is depicted in FIG. 8. In the embodiment shown in FIG. 8 a flap 40 is engaged to and disposed about both the distal side 80 as well as the proximal side 82 of the side branch opening 35.

In at least one embodiment when the stent 30 and flap 40 are fully deployed, a portion of the stent 30 and a portion of the flap 40 are overlappingly engaged and are both pushed against the contra-lateral wall 106.

Figure 3:
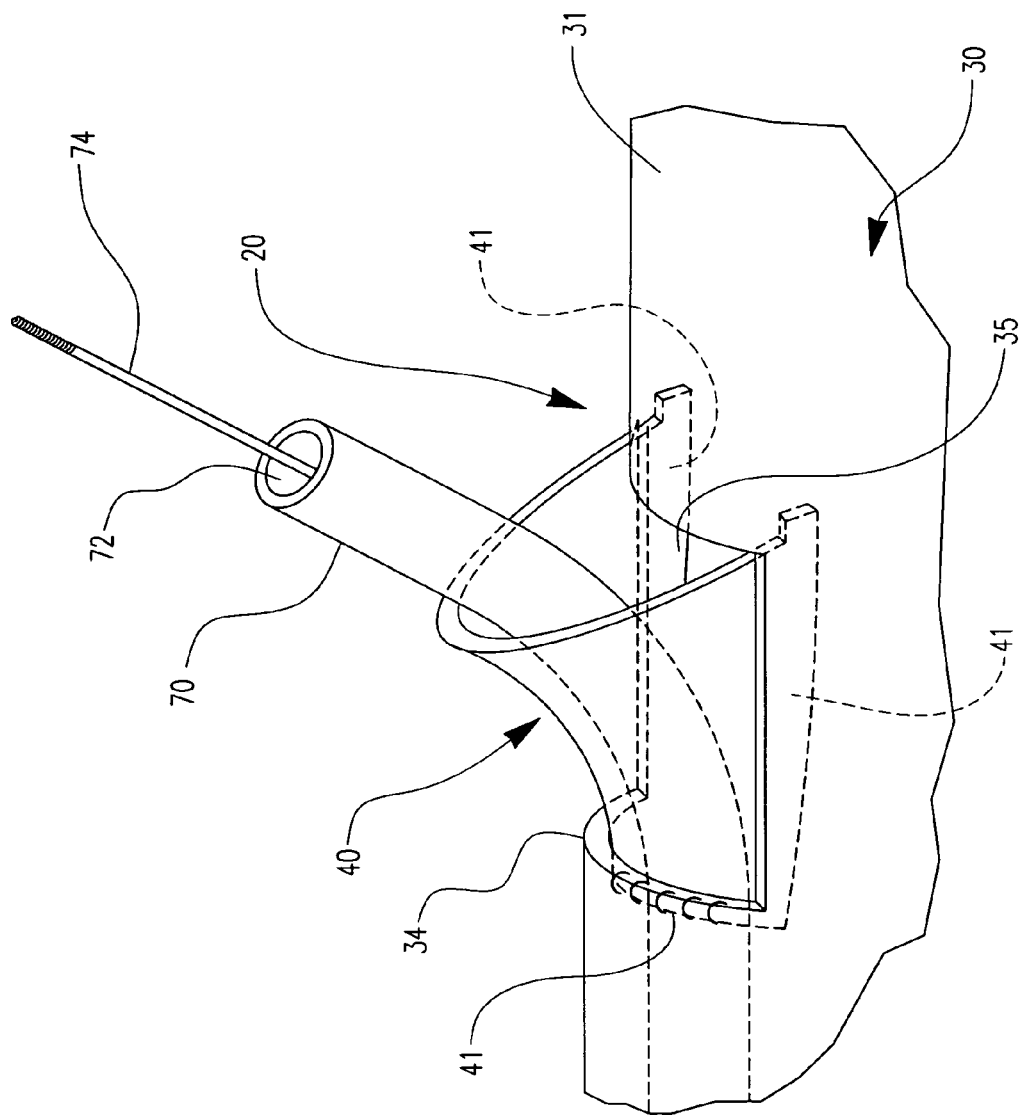
FIG. 3 is a partial perspective view of the stent assembly depicted in FIG. 1.

Unlike the tubular body of the stent 30, the flap 40 is a substantially planar structure which is prior to deployment is positioned immediately adjacent to the side branch opening 35 of the stent 30, such as in the manner depicted in FIGS. 1 and 3. During and subsequent to deployment, a portion of the flap 40 is take on a substantially cowl-like shape, such as is shown in FIG. 3, which extends radially outward from the stent 30.

Figure 4:
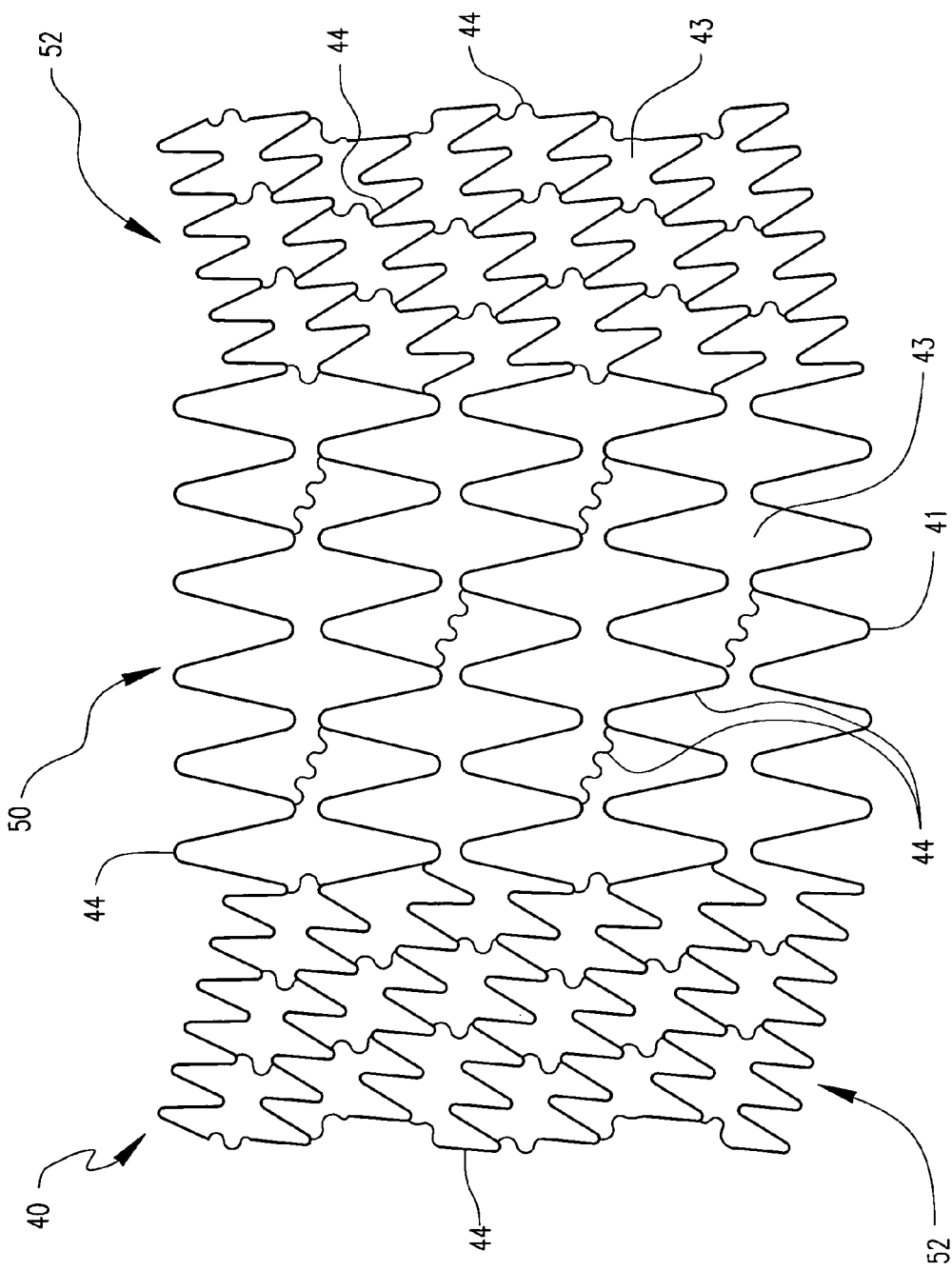
FIG. 4 is a detailed view of an embodiment of the flap section of the assembly shown in FIGS. 1 and 3.

In at least one embodiment, the flap 40, when viewed from 'above' as a two dimensional planar structure, has a somewhat frusto-conical or truncated conical shape, such as is shown in FIG. 4. When viewed in this manner the flap 40 has a plurality of sides 41 which define the plane of the flap. In the various embodiments of the invention at least one of the sides 41 of the flap is engaged to the body 31 or at least one stent member 34 which define the side-branch opening 35. In the embodiment depicted in FIGS. 1 and 3 for example, the flap 40 has at least three sides 41 which remain engaged to the body 31 of the stent 30 before, during, and after deployment of the assembly 20, such as in the manner depicted in FIGS. 1-3 and 6-7.

The flap 40 may be somewhat similar to the stent 30 in its construction, having a plurality of interconnected members, in this case, flap members 44, which define a plurality of flap cells 43. The configuration, pattern, size, shape, and/or other characteristics of the flap members 44 and flap cells 43 may be similar or different to the corresponding characteristics of the stent members 34 and stent cells 33, such as have been previously described. For example, as is shown in FIG. 4, the flap members 44 and the flap cells 43 define at least one visually recognizable pattern on the flap 40. This 'flap' pattern may be visually similar (or distinct) to (from) a pattern on the tubular body 31 of the stent 30, such as is defined by the stent members 34 and stent cells 33 in the manner previously described.

Such similar or differing geometry between the flap 40 and stent 30 may be selected to provide the assembly 20 with varying trackability, rigidity, flexibility, etc.

The stent and/or the flap may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The stent and/or the flap may be made of shape memory materials such as superelastic Nitinol or spring steel, or may be made of materials which are plastically deformable. In the case of shape memory materials, the stent and/or the flap may be provided with a memorized shape and then deformed to a reduced diameter shape. The stent and/or the flap may restore itself to its memorized shape upon being heated to a transition temperature and having any restraints removed therefrom.

The stent may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stent and/or the flap disclosed herein.

In some embodiments the stent and/or the flap, the delivery system or other portion may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In at least one embodiment, such as is depicted in FIG. 4, the flap 40 may be characterized as having at least two regions, referred to hereinafter as a branch region 50 and an engagement region 52, wherein the pattern of flap members 44 and/or flap cells 43 are different between regions. In the embodiment shown for example, the branch region has significantly larger cells 43 than the adjacent engagement regions 52. Alternatively, the branch region 50 can be characterized has having a lower density of flap members 44 than the adjacent engagement regions 52.

In at least one embodiment the wall thickness of the engagement region 52 is different than that of the branch region 50. For example, in some embodiments the wall thickness of the engagement region is thinner than the branch region 50.

One of ordinary skill in the art will recognize that by changing the construction, material composition, configuration, etc. of the regions of the of the flap 40, as well as the stent 30, the regions can be provided with any of a variety of similar or different expansion characteristics as may be desired.

For example, in the embodiment shown in FIG. 4, the branch region 50, is provided with a lower density of flap members 44 than the adjacent regions 52 so that the branch region 50 will have less resistance to expansion than the adjacent regions when a deployment force is exerted against the flap as a whole.

Deployment of the stent assembly 20 into a vessel bifurcation may be achieved in a variety of ways. In the embodiment shown in FIGS. 1, 5 and 6, the assembly 20 is incorporated into the stent delivery system 10 which is advanced to the bifurcation 104. The assembly 20 is positioned on a stent retaining region 60 of a stent delivery catheter 12 in a reduced diameter or predeployed state such as is shown. In at least one embodiment, where the stent 30 is a balloon expandable stent, the stent retaining region 60 is at least partially comprised of an expandable member or balloon 62.

Balloon 62 may be a typical angioplasty, stent delivery balloon or other inflatable member which may be used or incorporated into a catheter assembly. The balloon 62 may be constructed of any suitable balloon material known to those of skill in the art. Commonly employed materials include the thermoplastic elastomeric and non-elastomeric polymers and the thermosets including the moisture curable polymers.

Examples of suitable materials include but are not limited to, polyolefins, polyesters, polyurethanes, polyamides, polyimides, polycarbonates, polyphenylene sulfides, polyphenylene oxides, polyethers, silicones, polycarbonates, styrenic polymers, copolymers thereof, and mixtures thereof. Some of these classes are available both as thermosets and as thermoplastic polymers. See commonly assigned U.S. Pat. No. 5,500,181, for example, which is incorporated by reference herein in its entirety. As used herein, the term copolymer shall be used to refer to any polymeric material formed from more than one monomer.

As used herein, the term "copolymer" shall be used to refer to any polymer formed from two or more monomers, e.g. 2, 3, 4, 5 and so on and so forth.

Useful polyamides include, but are not limited to, nylon 12, nylon 11, nylon 9, nylon 6/9 and nylon 6/6. The use of such materials is described in U.S. Pat. No. 4,906,244, for example, the entire content of which is incorporated by reference herein in its entirety.

Examples of some copolymers of such materials include the polyether-block-amides, available from Elf Atochem North America in Philadelphia, Pa. under the tradename of PEBAX®. Another suitable copolymer is a polyetheresteramide.

Suitable polyester copolymers, include, for example, polyethyelene terephthalate and polybutylene terephthalate, polyester ethers and polyester elastomer copolymers such as those available from DuPont in Wilmington, Del. under the tradename of HYTREL®.

Block copolymer elastomers such as those copolymers having styrene end blocks, and midblocks formed from butadiene, isoprene, ethylene/butylene, ethylene/propene, and so forth may be employed herein. Other styrenic block copolymers include acrylonitrile-styrene and acrylonitrile-butadiene-styrene block copolymers. Also, block copolymers wherein the particular block copolymer thermoplastic elastomers in which the block copolymer is made up of hard segments of a polyester or polyamide and soft segments of polyether.

Specific examples of polyester/polyether block copolymers are poly(butylene terephthalate)-block-poly(tetramethylene oxide) polymers such as ARNITEL® EM 740, available from DSM Engineering Plastics. and HYTREL® polymers available from DuPont de Nemours & Co, already mentioned above.

The above materials are intended for illustrative purposes only, and not as a limitation on the scope of the present invention. Suitable polymeric materials available for use are vast and too numerous to be listed herein and are known to those of ordinary skill in the art.

Figure 6:
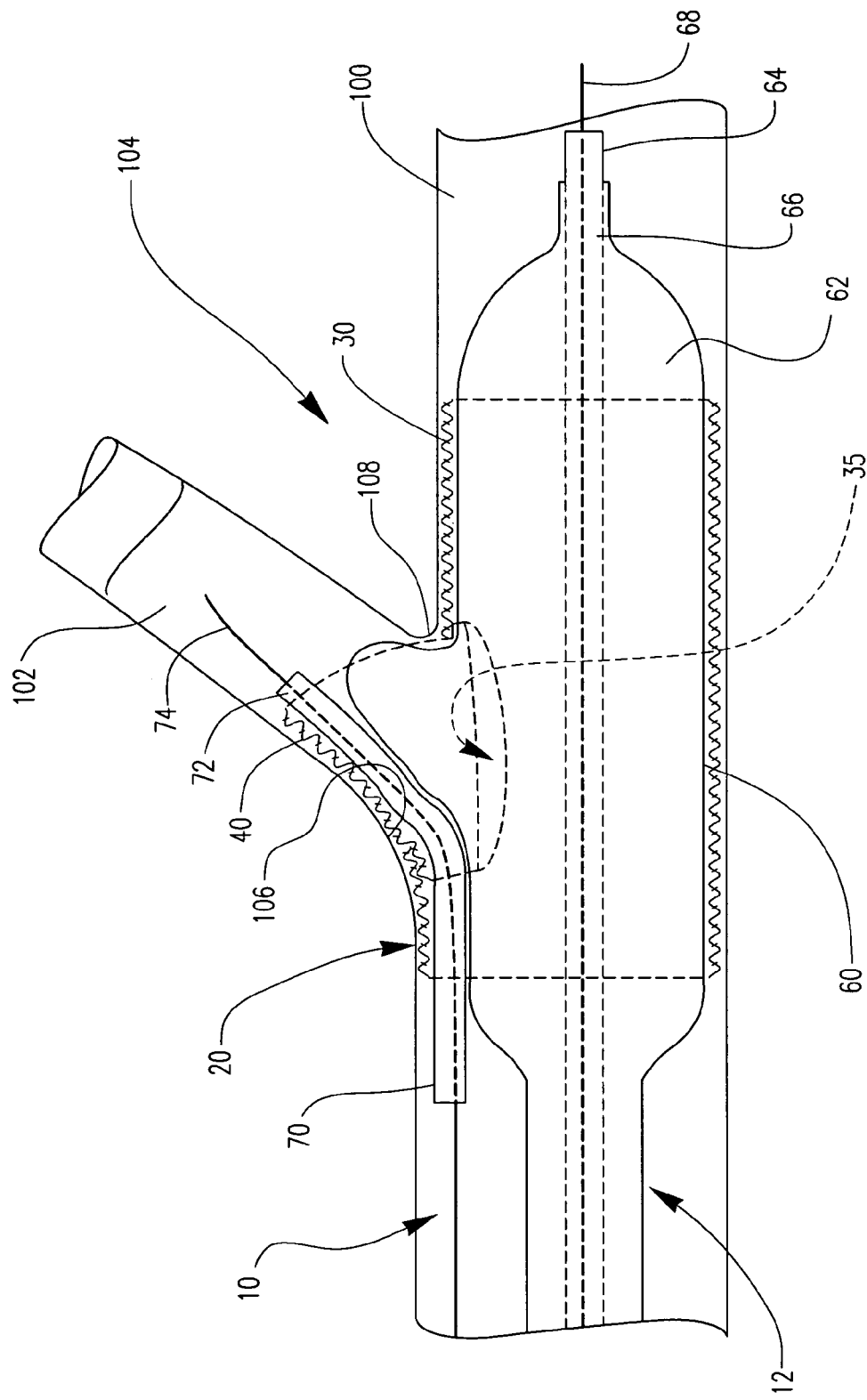
FIG. 6 is a longitudinal side, cross-sectional view of the embodiment shown in FIG. 1 wherein the assembly is shown being deployed.

By expanding the balloon 62 from a reduced, predeployed diameter to a greater, deployed diameter, such as is shown in FIG. 6, the balloon 62 will exert expansion or deployment forces upon the assembly 20. The expansion forces exerted on the assembly are sufficient to expand the assembly to its deployed state within the vessel bifurcation 104. Subsequent to the deployment of the assembly 20, the catheter is removed from the vessel 100 and the assembly 20 remains in place to support the bifurcation 104 such as in the manner shown in FIG. 7.

The system 10 may be advanced to the bifurcation 104 using various mechanisms. For example, in the embodiment shown in FIGS. 1, 5 and 6, the system 10 employs a catheter 12 which has a catheter shaft 64. Shaft 64 defines a guidewire lumen 66 through which a first or primary guidewire 68 may slidingly pass. In some embodiments the primary guidewire 68 is advanced through the primary vessel 100 and across the bifurcation 104. By advancing the catheter 12 along the guidewire 68 the system is advanced through the primary vessel 100.

Alternatively the catheter 12 may be a fixed wire catheter or other type of catheter that is capable of being advanced through the vasculature or other body lumen(s).

As the assembly 20 is intended for deployment at a vessel bifurcation 104, in at least one embodiment the system 10 includes one or more mechanisms for aligning the side branch opening of the stent with the ostium of the secondary vessel.

In the embodiment shown, the system 10 includes a secondary guidewire housing 70 which defines a secondary guidewire lumen 72. The secondary guidewire lumen 72 is constructed and arranged to permit sliding passage of a secondary guidewire 74 therethrough. The secondary guidewire housing 74 may be constructed from any flexible tubular structure suitable for use of tracking along a guidewire.

In some embodiments the secondary guidewire housing is a tube of material, wherein the material is selected from the group including: PEBAX, peek, polyimide, etc. In at least one embodiment the housing is a braided tube of metal wire or other material, a hypotube having slots or other mechanisms to provide flexibility, or other flexible tubular device.

In some embodiments the secondary guidewire 74 is advanced through the primary vessel 100 and at the bifurcation 104 is advanced into the secondary vessel 102. Once the primary guidewire 68 is in place within the primary vessel 100 and the secondary guidewire 74 is positioned to extend into the secondary vessel 102 such as in the manner shown in FIG. 1, the system 10 may be advanced along both wires simultaneously.

In the embodiment shown in FIGS. 1 and 3, the secondary guidewire housing 70 extends through the proximal portion of the stent 32 lumen and exits the stent 30 through the side-branch opening 35. This configuration allows the secondary guidewire housing 70 to provide a torquing affect on the system 10 as it is advanced toward the bifurcation 104 along both guidewire. As a result the side branch opening 35 will be rotated into alignment with the secondary vessel 102.

Once the system is aligned in the manner shown in FIG. 1, the assembly 20 may be deployed in the manner previously described.

Figure 5:
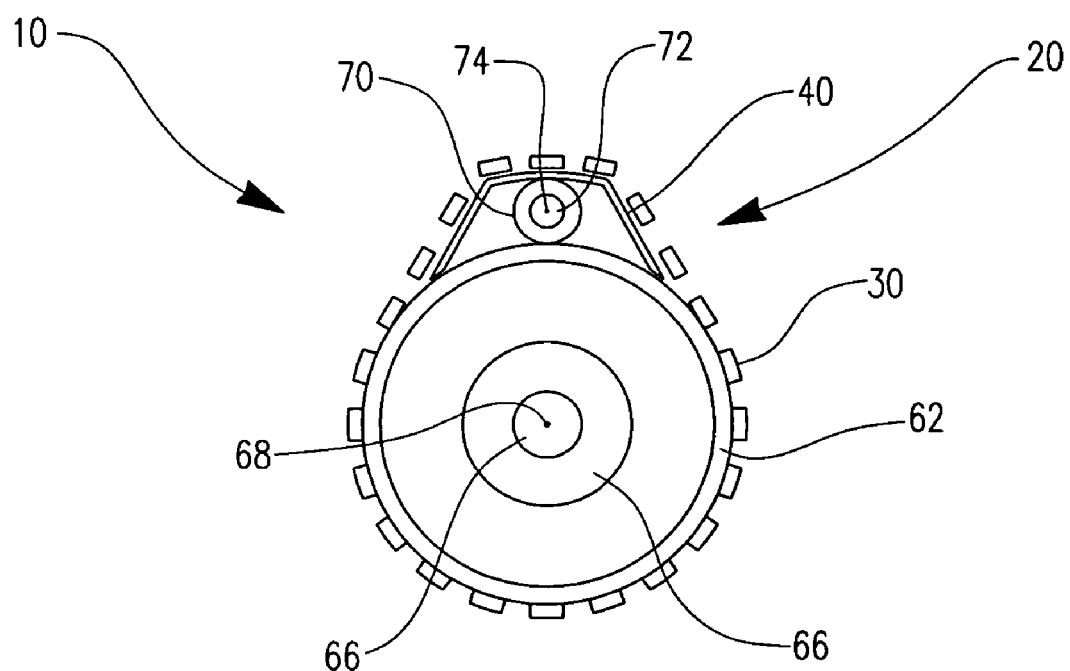
FIG. 5 is transverse cross-sectional view of a region of the embodiment shown in FIG. 1.

In at least one embodiment, an example of which is shown in FIG. 5 the flap 40, prior to deployment, is positioned directly over the balloon 62 and the portion of the secondary guidewire housing 70 adjacent to the side branch opening 35. In this configuration the branch region 50 of the flap 40 is immediately radially adjacent or 'on top' of the secondary guidewire housing 70 and the surrounding regions 52 of the flap are radially position upon the balloon 62. The sent 30 is then mounted over the flap 40, balloon 62 and housing 70 in the manner previously shown and described.

In at least one embodiment the side branch opening 35 is substantially crossed by the flap 40, but there is sufficient area remaining to allow the secondary guidewire housing 70 to exit the side branch opening 35 as well.

In at least some embodiments, at least a portion of the flap 40, such as the branch region 50 which covers at least a portion of the side branch opening 35 prior to delivery, is particularly flexible. This highly flexible region of the flap 40 permits at least the branch region 50 of the flap to be distended into a cowl-like shape which is pushed 'upward' or radially outward from the stent 20 as the secondary guidewire housing 70 tracks along the secondary guidewire 74 and into the secondary vessel 102, such as in the manner shown in FIGS. 1 and 3.

The distention or biasing of the branch region 50 of the flap 40 provides a number of benefits. For example, where the flap 40 is made to be radiopaque, the distention of the flap 40 will indicate to an operator that the side branch opening 35 of the stent 30 is actually aligned with the ostium of the secondary vessel, before the assembly is expanded for delivery. Furthermore, the flap 40 will act as a break on the system 10 halting the advancement of the system 10 at is pushed against the carina 108 of the bifurcation 104.

When the system 10 is positioned in the manner shown in FIG. 1, the balloon 62 is expanded to deploy the assembly 20 in the manner shown in FIG. 6.

While a balloon having traditional or somewhat uniform expansion characteristics may be used in some embodiments of the invention to deploy the assembly 20, in at least one embodiment at least a portion of the balloon adjacent to the side branch opening 35 has different expansion characteristics than the remainder of the balloon. In a least one embodiment this portion of the balloon adjacent to the side branch opening 35 is configured to push outward through the opening 35 to act upon the secondary guidewire housing 70 and or the flap 40 directly when the balloon is expanded.

In some embodiment a therapeutic agent may be placed on the stent 30, flap 40 and/or other portion of the assembly 10 in the form of a coating. Often the coating includes at least one therapeutic agent and at least one polymer.

In embodiments where the assembly comprises one or more therapeutic agents, an agent or agents present on the stent 30 may be similar or different to the agent or agents which may be present on the flap 40. The dosage of the agents on the stent and/or flap may vary or be different on different portions of the assembly.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

With this description, those skilled in the art may recognize other equivalents to the specific embodiment described herein. Such equivalents are intended to be encompassed by the claims attached hereto.

The invention claimed is:

1. A stent assembly having an undeployed state and a deployed state, the assembly comprising:
   a stent, the stent comprising a substantially tubular body, the body having a longitudinal axis, the body having an inner surface and an outer surface, the inner surface of the body defining a primary lumen, the body being comprised of a plurality of interconnected stent members, adjacent stent members defining a plurality of stent openings that extend through the body in fluid communication with the primary lumen, at least one stent opening being a side branch opening, the side branch opening having a perimeter; and
   a side branch flap, the side branch flap comprising a non-tubular body,
   in the undeployed state a first region of the non-tubular body is overlappingly positioned across at least a portion of the side branch opening, a second region of the non-tubular body is engaged to a portion of the inner surface of the body of the stent immediately adjacent to the perimeter of the side branch opening,
   in the deployed state the first region is displaced radially outward from the at least a portion of the side branch opening, and
   wherein the non-tubular body of the side branch flap is defined by at least three sides, at least three of the sides remaining engaged to the portion of the body of the stent immediately adjacent to the perimeter of the side branch opening in both the undeployed state and the deployed state.

2. The assembly of claim 1 wherein at least a portion of the first region has a substantially cowl-like shape in the deployed state.

3. The assembly of claim 1 wherein the flap members of at least a portion of the second region of the side branch flap are interlocked with the stent members of the body of the stent immediately adjacent to the perimeter of the side branch opening.

4. The assembly of claim 1 wherein the side branch flap is constructed of a plurality of interconnected flap members, wherein adjacent flap members define flap openings therebetween, the interconnected flap members and flap openings define a visibly recognizable flap pattern.

5. The assembly of claim 4 wherein the flap pattern in the first region is visibly distinct from the flap pattern in the second region.

6. The assembly of claim 4 wherein the plurality of interconnected stent members and stent openings define a visibly recognizable stent pattern, the stent pattern being substantially similar to that of the flap pattern.

7. A stent delivery system for delivering a stent assembly to a vessel bifurcation, the system comprising:
   a catheter, the catheter having a catheter shaft, a region of the catheter shaft comprising a stent retaining region;
   a stent, the stent having an undeployed state and a deployed state, in the undeployed state the stent being disposed about the stent retaining region, the stent having a tubular body, the body having an inner surface and an outer surface, the inner surface defines a primary lumen therethrough, the body further defining at least one side branch opening in fluid communication with the primary lumen; and
   a side branch flap, the side branch flap comprising a non-tubular body, in the undeployed state a first region of the non-tubular body is overlappingly positioned across at least a portion of the side branch opening and a second region of the non-tubular body is engaged to a portion of the inner surface of the body of the stent immediately adjacent to the side branch opening and within the primary lumen, and
   wherein the non-tubular body of the side branch flap is defined by at least three sides, at least three of the sides remaining engaged to the portion of the body of the stent immediately adjacent to the perimeter of the side branch opening in both the undeployed state and the deployed state.

8. The system of claim 7 wherein at least a portion of the first region of the flap comprises a substantially cowl-like shape over the side branch opening of the stent.

9. The system of claim 7 wherein the catheter shaft defines a primary guidewire lumen.

10. The system of claim 7 wherein at least a portion of at least one of the stent and side branch flap comprise at least one therapeutic agent.

11. The system of claim 7 further comprising:
a side branch guide housing, the side branch guide housing comprising a tubular member defining a secondary guidewire lumen therethrough, the side branch guide housing positioned adjacent to the stent retaining region of the catheter shaft, a first portion of the guide housing extending within a proximal portion of the primary lumen and exiting the primary lumen through the side branch opening, at least a portion of the side branch flap positioned between the stent and the side branch guide housing.

12. The system of claim 11 wherein at least a portion of the stent retaining region comprises an expandable balloon.

13. The system of claim 12 wherein in the undeployed state at least a portion of the first region of the non-tubular body is positioned immediately radially adjacent to the side branch guide housing.

14. The system of claim 13 wherein in the undeployed state the stent is disposed about the balloon, at least a portion of the flap being frictionally engaged between the balloon and the portion of the body of the stent immediately adjacent to the side branch opening.

15. A method of treating a vessel bifurcation comprising the steps of:
advancing a first guidewire through a first vessel, such that the first guidewire extends proximally beyond a bifurcation of the first vessel and a second vessel;
advancing a second guidewire through the first vessel to the bifurcation and into the second vessel;
providing a stent delivery system, the system comprising:
a catheter, the catheter having a catheter shaft, the catheter shaft defining a first guidewire lumen for sliding passage of the first guidewire therethrough, a region of the catheter shaft comprising a stent retaining region;
a stent, the stent having an undeployed state and a deployed state, in the undeployed state the stent being disposed about the stent retaining region, the stent having a tubular body, the body having an inner surface and an outer surface, the inner surface defines a primary lumen therethrough, the body further defining at least one side branch opening in fluid communication with the primary lumen;
a side branch flap, the side branch flap comprising a non-tubular body, in the undeployed state a first region of the non-tubular body is overlappingly positioned across at least a portion of the side branch opening and a second region of the non-tubular body is engaged to a portion of the inner surface of the body of the stent immediately adjacent to the side branch opening and within the primary lumen, wherein the non-tubular body of the side branch flap is defined by at least three sides, at least three of the sides remaining engaged to the portion of the body of the stent immediately adjacent to the perimeter of the side branch opening in both the undeployed state and the deployed state; and
a secondary guidewire housing, the secondary guidewire housing comprising a tubular member defining a second guidewire lumen for sliding passage of the second guidewire therethrough, the secondary guidewire housing positioned adjacent to the stent retaining region of the catheter shaft, a first portion of the secondary guidewire housing extending within a proximal portion of the primary lumen and exiting the primary lumen through the side branch opening, at least a portion of the side branch flap positioned between the stent and the secondary guidewire housing;
advancing the stent delivery system along the first guidewire and the second guidewire through the first vessel;
rotationally aligning the side branch opening of the stent with the second vessel;
pushing at least a portion of the first region of the side branch flap into the secondary vessel by advancing a distal portion of the secondary guidewire housing along the second guidewire and into the second vessel;
expanding the stent and the side branch flap from the undeployed state to the deployed state, such that the at least a portion of the first region of the side branch flap is positioned immediately adjacent a contra-lateral wall of the second vessel.

* * * * *